Figure 1:
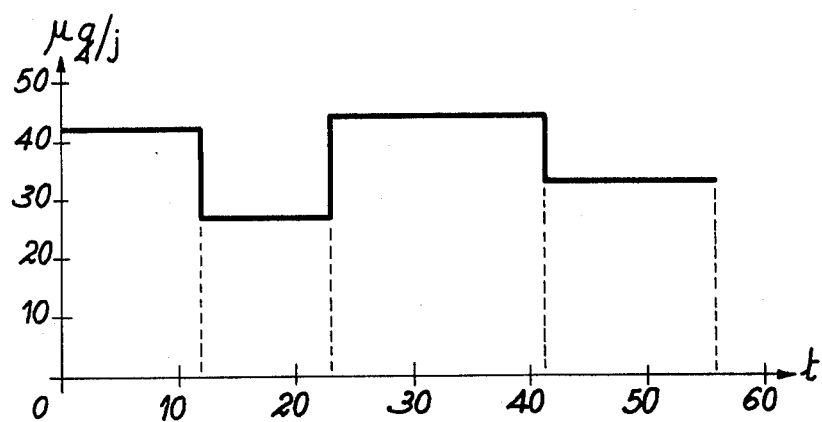

United States Patent [19]
Berthet et al.

[11] 4,283,325
[45] Aug. 11, 1981

[54] HYDROPHOBIC SUBSTRATE WHICH IS ABLE TO RELEASE A CHEMICAL SUBSTANCE

[75] Inventors: Jeanne Berthet, Velizy Villacoublay; Gilbert Gaussens, Meudon, both of France

[73] Assignee: Commissariat a l'Energie Atomique, Paris, France

[21] Appl. No.: 66,521

[22] Filed: Aug. 15, 1979

[30] Foreign Application Priority Data

Aug. 25, 1978 [FR] France ............................... 78 24678

[51] Int. Cl.$^3$ .............................................. A61F 5/46
[52] U.S. Cl. .................................. 260/37 M; 128/130; 260/40 R; 260/42.22; 424/78; 424/79; 424/81; 424/82; 424/83; 424/DIG. 14; 525/63; 525/64; 525/71
[58] Field of Search ............... 260/37 M, 40 R, 42.22; 128/130; 424/DIG. 14, 78, 79, 81, 82, 83; 525/63, 64, 71

[56] References Cited
U.S. PATENT DOCUMENTS 3,803,308  4/1974  Zipper .................................. 424/140

FOREIGN PATENT DOCUMENTS 1456775  11/1976  United Kingdom ..................... 128/130

Primary Examiner—Ronald W. Griffin
Attorney, Agent, or Firm—Thomas R. Boland

[57] ABSTRACT

Hydrophobic substrate which can release at least one chemical substance, wherein it comprises a hydrophobic polymer matrix in which are homogeneously distributed inclusions of polymerized compounds of a different type to the said hydrophobic polymer and inclusions of the said substance, the polymerized compound inclusions forming in the said matrix a stable and continuous system in contact with the inclusions of the said substance.

Process for the preparation of a hydrophobic substrate able to release a chemical substance, wherein it comprises forming inclusions of polymerized compounds in a hydrophobic polymer powder by grafting onto the latter a monomer of a different type to the said hydrophobic polymer, homogeneously mixing the grafted powder obtained in this way with a powder of the said substance and bringing the mixture into the form of a substrate by hot shaping it.

26 Claims, 10 Drawing Figures

HYDROPHOBIC SUBSTRATE WHICH IS ABLE TO RELEASE A CHEMICAL SUBSTANCE

BACKGROUND OF THE INVENTION

The present invention relates to a hydrophobic substrate which is able to release a chemical substance and to a process for producing such a substrate.

Substrates are known which have the property of being able to release a chemical substance at a controlled speed for an extended period and such substrates are of great interest in numerous fields, particularly in the medical field.

Thus, such substrates can be used for the introduction into the human body of an active substance such as a medicament and a particular use thereof is in intrauterine devices which are able to release into the uterus during an extended period a substantially constant dose of an active substance such as a contraceptive agent.

The presently known processes for preparing substances of this type involve the formation in a first stage of hydrophilic or hydrophobic inclusions in a hydrophobic substrate, whilst the second stage consists of the absorption of a chemical substance in the hydrophilic or hydrophobic inclusions of the substrate.

In the substrates obtained by such processes the quantity of chemical substance stored in the substrate is limited by the number of hydrophilic or hydrophobic inclusions in the substrate and by the absorption capacity of the polymer constituting these inclusions. In addition, for certain applications such substrates have the disadvantage of containing an inadequate quantity of chemical substance.

BRIEF SUMMARY OF THE INVENTION

The present invention relates to a hydrophobic substrate which is able to release a chemical substance and which has the advantage of being able to contain a larger quantity of chemical substance than the presently known substrates.

According to the invention, the hydrophobic substrate which is able to release at least one chemical substance comprises a hydrophobic polymr matrix in which are homogeneously distributed inclusions of polymerized compounds which differ from the hydrophobic polymer and inclusions of the said substance, the polymerized compound inclusions forming in the matrix a stable and continuous system in contact with the inclusions of said substance.

The hydrophobic substrate as defined hereinbefore takes advantage of its special structure making it possible to release, i.e. under certain conditions, the chemical substance contained therein due to the presence of the stable system of polymerized compound inclusions, which constitutes within the hydrophobic polymer matrix an access route to the inclusions of the chemical substance.

According to a first embodiment of the invention, the inclusions of polymerized compounds are inclusions of hydrophilic compounds, for example inclusions of polymers of a hydrophilic monomer chosen from the group containing acrylamide, ethylene glycol acrylate, methylol acrylamide, diacetone acrylamide, maleic acid, acrylic acid, fumaric acid, itaconic acid, propylene glycol acrylate, ethylene glycol methacrylate, methacrylamide, methacrylic acid and propylene glycol methacrylate.

This embodiment is particularly advantageous for the release of chemical substances into a polar solution, due to the fact that hydrophilic inclusions have the property of absorbing polar solutions.

Thus, when such a substrate is submerged in a polar solution, the latter can penetrate the hydrophobic polymr matrix following the path of the hydrophilic inclusions and comes into contact with the chemical substance inclusions, thereby reacting with said chemical substance for solubilizing it and then finally migrating to the exterior of the substrate also following the path to the hydrophilic inclusions in order to release the substance outside the substrate.

In this first embodiment of the invention, the chemical substance is advantageously a metal or a metal salt such as copper or copper acetate.

According to a second embodiment of the invention, the inclusions of polymerized compounds are inclusions of hydrophobic compounds for example polymer inclusions of a hydrophobic monomer chosen from the group containing ethyl acrylate, butyl acrylate, isobutyl acrylate, hexyl acrylate, heptyl acrylate, ethyl methacrylate, butyl methacrylate, isobutyl methacrylate, hexyl methacrylate, heptyl methacrylate and acrylonitrile.

This second embodiment of the invention is particularly advantageous for the release of a chemical substance into a medium which can be absorbed by the hydrophobic inclusions.

In this case, when such a substrate is brought into contact with the appropriate medium, the latter can penetrate the hydrophobic polymer matrix following the path of the hydrophobic inclusions in order to come into contact with the chemical substance inclusions, after which it reacts with the chemical substance or solubilizes it and finally migrates to the exterior of the substrate also following the path of the hydrophobic inclusions in order to release the substance outside the substrate.

In these two embodiments of the invention, the hydrophobic polymer of the matrix is advantageously chosen from the group containing polyvinyl acetates, polyethylenes, polypropylenes, polyamides, ethylene glycol polyterephthalate, polyvinylchlorides, polyformaldehyde chlorides, polycarbonates, ethylene copolymers, polyethers, polyurethanes, polyacrylonitriles and copolymers of polyethylene and vinylacetate.

The present invention also relates to a process for preparing a hydrophobic substrate able to release a chemical substance.

This process comprises:

(a) forming in a hydrophobic polymer powder inclusions of polymerised compounds by grafting a monomer of a different nature to the said hydrophobic polymer on the hydrophobic polymer powder (b) homogeneously mixing the thus obtained grafted powder with a powder of the said substance and (c) bringing the mixture into the form of a substrate by hot shaping it.

The processes defined hereinbefore takes advantage of the fact that by creating polymerized compound inclusions by grafting in a hydrophobic polymer powder and by then subjecting a mixture of the grafted powder and the chemical substance powder to a hot shaping operation a substrate is obtained having a hydrophobic polymer matrix in which are distributed chemical substance inclusions and polymerized compound inclusions which, due to the presence of the covalent bonds formed during grafting form within the matrix a stable system in contact with the inclusions of the chemical substance.

According to the invention, the grafting of the monomer onto the hydrophobic polymer powder can be obtained by any known process, for example chemically or by irradiation by means of ionizing radiation such as X, gamma or ultraviolet rays or by an electron beam.

According to the invention, the grafting of the said monomer onto the said hydrophobic polymer powder is preferably obtained by subjecting the hydrophobic polymer powder immersed in a solution of the monomer containing the polymerization inhibitor to irradiation by means of ionizing rays.

In this embodiment, the grafting level of the monomer on the hydrophobic polymer is controlled by regulating the temperature and monomer concentration of the solution, the irradiation dose flow rate and the irradiation duration.

The degree of grafting is selected as a function of the nature of the hydrophobic polymer and the monomer used for grafting purposes in such a way that the substrate obtained has a sufficient quantity of polymerized compound inclusions, whilst also having the interesting mechanical properties of the hydrophobic matrix, for example the mechanical flexibility when the substrates are to be used as intrauterine devices.

After grafting, the grafted powder is intimately mixed with a powder of the chemical substance to be stored in the substrate. This operation can be performed in a conventional powder mixer, for example a Moritz mixer.

The chemical substance powder used for making the mixture preferably has a grain size below that of the grafted hydrophobic polymer powder in order to obtain a fine and homogeneous dispersion of the chemical substance in the hydrophobic polymer matrix.

The mixture obtained is then brought into the form of a substrate by hot shaping, for example by extrusion, injection moulding or compression moulding at a temperature below the melting temperature of the chemical substance.

In certain cases, following the hot shaping, the substrate obtained undergoes cross-linking by means of ionizing radiation.

Thus, if the migration rate of the chemical substance through the inclusions of the polymerized compounds is too high, it can be adjusted by carrying out cross-linking by irradiating the inclusions after the shaping operation. Obviously, for this purpose, the chemical substance must be able to withstand the irradiation.

According to the invention, the hydrophobic polymer is advantageously chosen from the group containing polyvinyl acetates, polyethylenes, polypropylenes, polyamides, ethylene glycol polyterephthalate, polyvinyl chlorides, polyformaldehyde chlorides, polycarbonates, ethylene copolymers, polethers, polyurethanes, polyacrylonitriles and copolymers of polyethylene and vinyl acetate.

According to the process of the invention, the monomer used for grafting purposes is a hydrophilic monomer such as acrylamide, ethylene glycol acrylate, methylol acrylamide, diacetone acrylamide, maleic acid, acrylic acid, fumaric acid, itaconic acid, propylene glycol acrylate, ethylene glycol methacrylate, methacrylamide, methacrylic acid and propylene glycol methacrylate, or a hydrophobic monomer such as ethyl acrylate, butyl acrylate, isobutyl acrylate, hexyl acrylate, heptyl acrylate, ethyl methacrylate, butyl methacrylate, isobutyl methacrylate, hexyl methacrylate, heptyl methacrylate and acrylonitrile.

According to the invention, when the monomer used for grafting is a hydrophilic monomer, the chemical substance is preferably a substance soluble in polar solution or a substance which reacts with a polar solution.

Examples of substances which can be used are in particular metals such as copper and metal salts which are soluble in water or in a polar solution, such as copper acetate. It is also possible to use active substances and in particular medicaments, obviously provided that they are solid at ambient temperature and remain stable at the temperature used for shaping the substrate.

It is pointed out that according to the process of the invention, the hydrophobic polymer and the monomer used for grafting are selected as a function of the nature and properties of the chemical substances to be stored in the substrate in such a way as to give the substrate obtained the property of being able to release the substance into an appropriate medium, for example into a gas, a polar solution or a non-polar liquid medium.

The hydrophobic polymer is selected as a function of its mechanical and chemical properties, bearing in mind the subsequent use of the substrate obtained. Thus, in the case of using the substrate as an intrauterine device, a hydrophobic polymer with a very considerable mechanical flexibility is used.

DESCRIPTION OF DRAWING AND PREFERRED EMBODIMENTS

The invention will be described in greater detail hereinafter relative to the illustrative and non-limitative examples and with reference to the attached drawings, wherein show:

FIG. 1 a graph of the quantity of copper released daily, as a function of time, by the substrate obtained in example 1, when the latter is brought into contact with a solution whose pH is adjusted to 6.5 at a temperature of 37° C.

Figure 2:
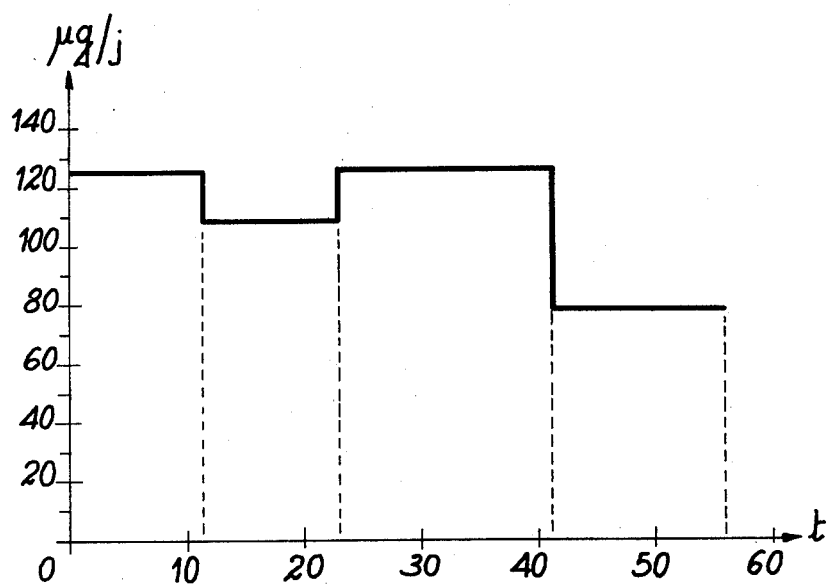

FIG. 2 a graph, as a function of time, of the quantity of copper released daily by the substance obtained in example 1, when the latter is brought into a contact with a solution whose pH is adjusted to 5 at a temperature of 37° C.

Figure 3:
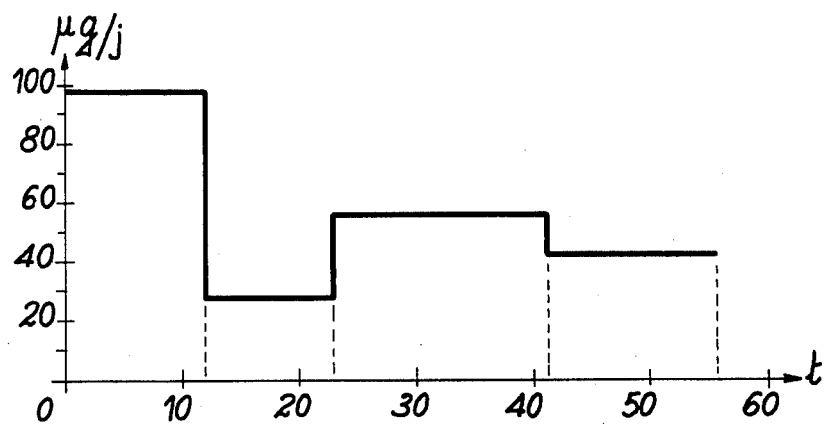

FIG. 3 a graph, as a function of time, of the quantity of copper released daily by the substance obtained in example 2, when the latter is brought into contact with a solution whose pH is adjusted to 6.5 at a temperature of 37° C.

Figure 4:
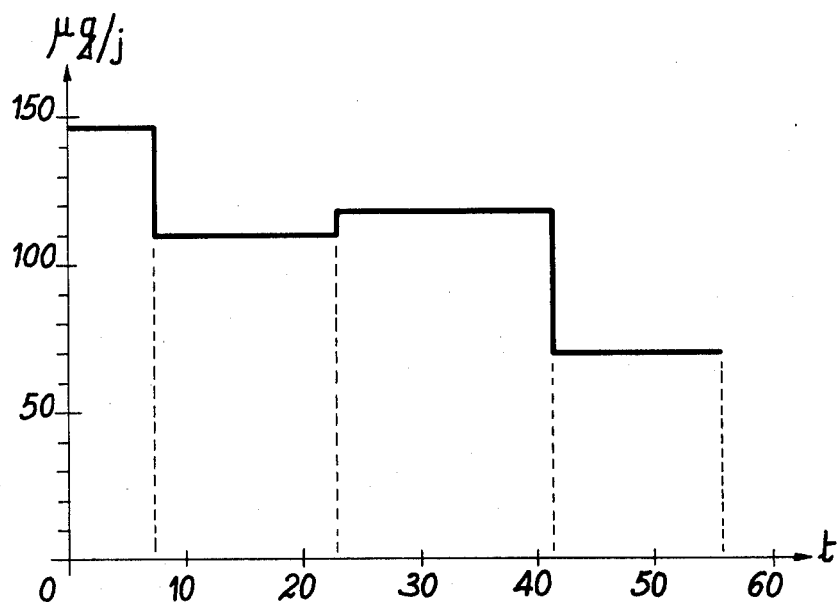

FIG. 4 is a graph, as a function of time, of the quantity of copper released daily by the substance obtained in example 2, when the latter is brought into contact with an aqueous solution whose pH has been adjusted to 5 at a temperature of 37° C.

Figure 5:
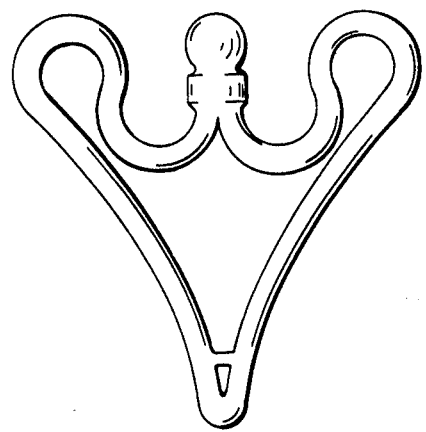

FIG. 5 a diagrammatic view of an intrauterine device.

Figure 6:
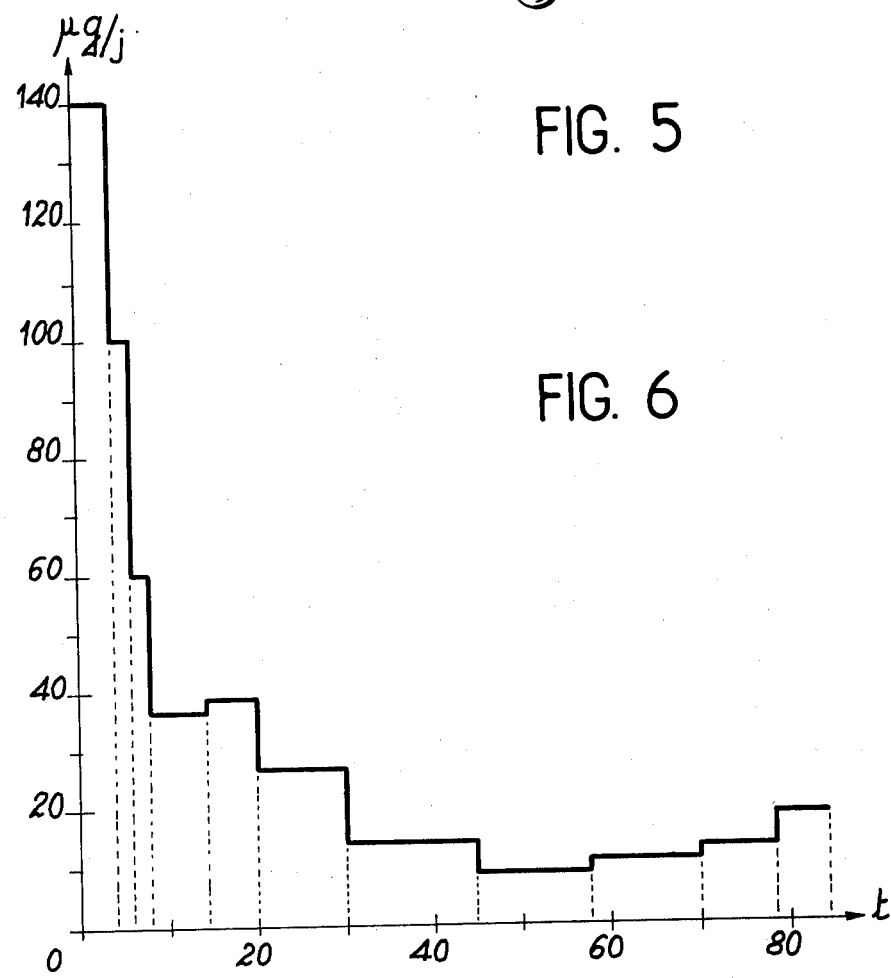

FIG. 6 a graph, as a function of time, of the quantity of copper released daily by the size 0 intrauterine device obtained in example 3 when said device is brought into contact with a solution whose pH has been adjusted to 6.4 at a temperature of 37° C.

Figure 7:
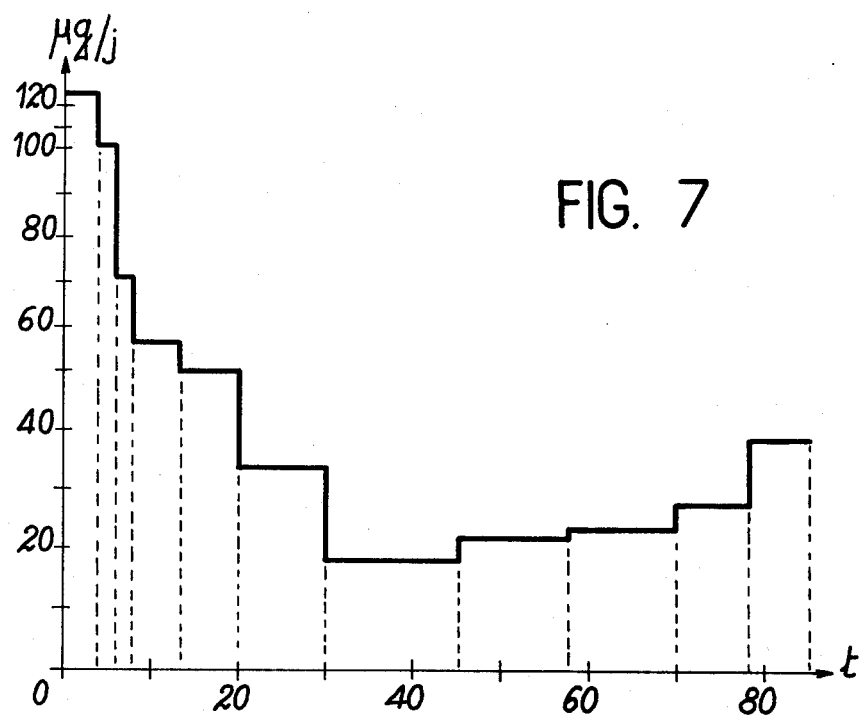

FIG. 7 a graph, as a function of time, of the quantity of copper released daily by the size 0 intrauterine device obtained in example 3 when this device is brought into contact with a solution whose pH has been adjusted to 5 at a temperature of 37° C.

Figure 8:
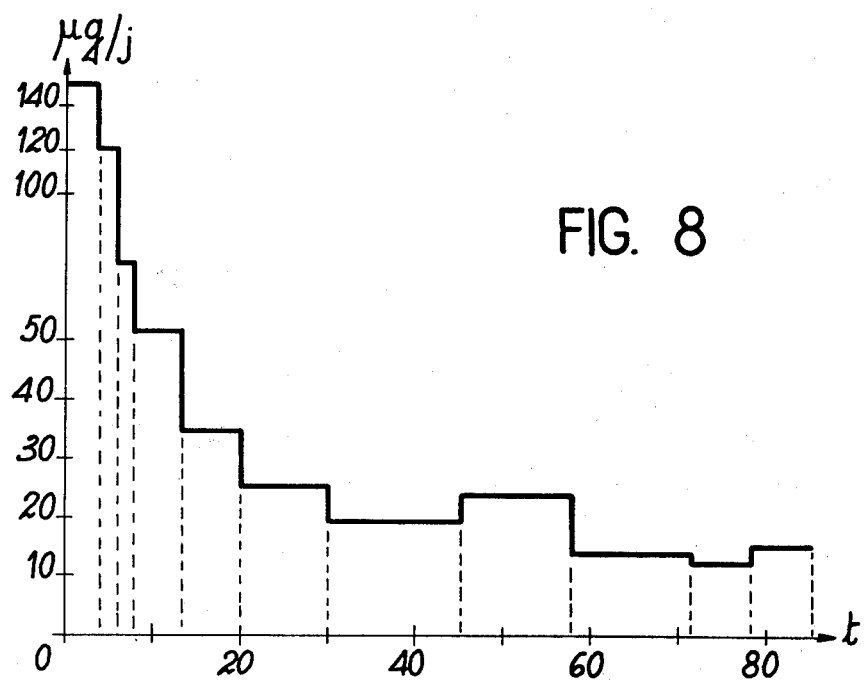

FIG. 8 a graph, as a function of time, of the quantity of copper released daily by the size 1 intrauterine device obtained in example 3 when said device is brought into contact with a solution whose pH has been adjusted to 6.5 at a temperature of 37° C.

Figure 9:
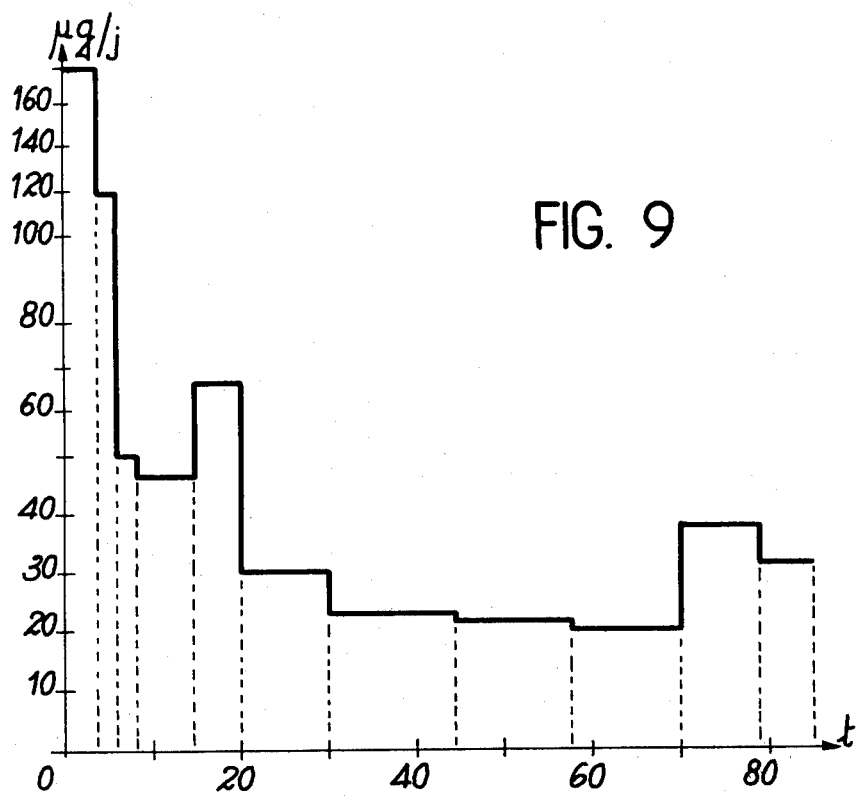

FIG. 9 a graph, as a function of time, of the quantity of copper released by a size 1 intrauterine device obtained in example 3, when the latter is brought into contact with a solution whose pH has been adjusted to 5 at a temperature of 37° C.

Figure 10:
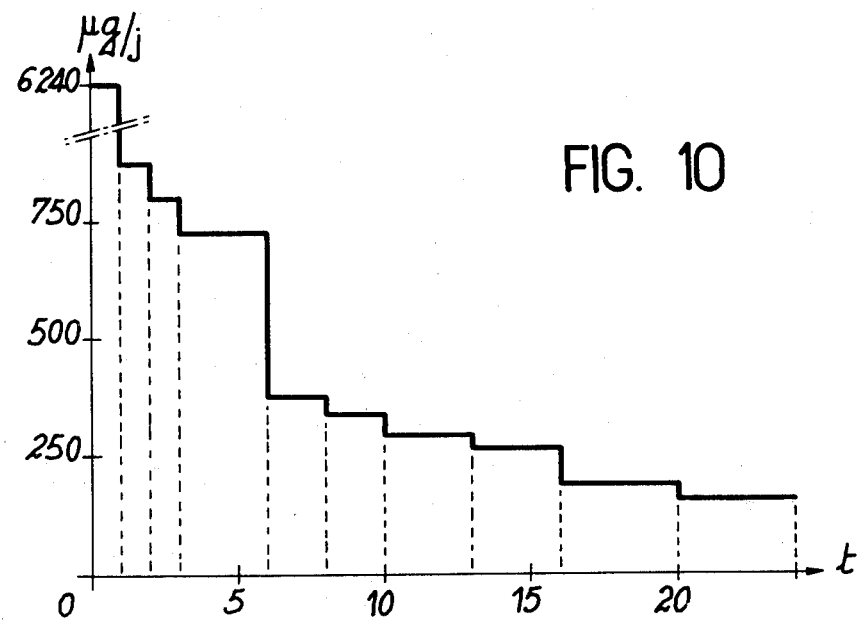

FIG. 10 a graph, as a function of time, of the quantity of copper released daily by the substrate obtained in example 4, when the latter is brought into contact with the solution whose pH has been adjusted 5 at a temperature of 37° C.

EXAMPLE 1

An ethylene/vinyl acetate copolymer (EVA) powder containing 33% by weight vinyl acetate is grafted using the following solution:

acrylic acid: 62.5 ml
soft water: 500 ml
Mohr's salt: 11 g (polymerization inhibitor)

Grafting is carried out by subjecting 125 g of the EVA copolymer powder with an average grain size of 1 mm, submerged in a grafting solution and accompanied by stirring, to irradiation by gamma rays by means of a cobalt 60 source at a dosage rate of 0.72 mrad/h for 1½ hours under a nitrogen atmosphere and a temperature of 20° C.

After irradiation, the grafted powder is washed and then dried in a vacuum oven. In this way, an acrylic acid-grafted copolymer powder is obtained whose degree of grafting is defined by the formula:

$$(P - Po) \times 100/Po$$

inwhich P stands for the weight of the powder after grafting and Po the weight of the powder before grafting is 36% by weight compared with the weight of the copolymer (EVA).

The grafted powder is then mixed with 12.5% by weight, based on the grafted powder weight, of copper powder with an average grain size of 50 microns at a temperature of 140° to 150° C. in a mixer and the mixture is then introduced into a 1 mm thick mould, whose plates are maintained at a temperature of 170° C.

The desorption properties of the thus prepared substrate are checked after cutting from the sheet obtained a portion with a surface area of 600 mm$^2$, i.e. an area which substantially corresponds to the area of a conventional intrauterine device. To this end, the sheet portion is submerged in 1 liter of isotonic solution (9 g of NaCl/l) maintained at a temperature of 37° C. and whose pH is adjusted to 5 or 6.5 by adding lactic acid in order to bring about a desorption of the copper in the solution. The solution is changed at regular intervals and the quantity of copper released into each of the sample solutions is checked by spectrophotometry of the copper dithizonate complex.

The results obtained are given in FIGS. 1 and 2 which respectively relate to the use of a solution with a pH of 6.5 and a solution with pH of 5.

On the basis of these graphs based on time (in days) of the quantity of copper ($\mu$g) released daily into the solution, it can be seen that the substrate obtained is able to release every date substantially constant quantities of copper. It can also be seen that the use of a more acid solution leads to an increase in the quantity of copper released every day.

EXAMPLE 2

In the same way as in Example 1, a copper powder-charged hydrophobic substrate is prepared by grafting acrylic acid onto an ethylene/vinyl acetate copolymer powder identical to that of example 1 by using the same grafting solution and the same irradiation dose rate as in example 1, but in this case irradiation is carried out for 43 minutes instead of 90 minutes.

The grafted powder obtained has a grafting degree of 30.4% by weight of acrylic acid, based on the EVA copolymer powder weight. As in example 1, the grafted powder is then mixed with 12.5% by weight of copper powder and the mixture is brought into the form of a 1 mm thick sheet by using the same operating procedure as in example 1, but by maintaining the mould plates at a temperature of 150° C. instead of 170° C.

The desorption properties of the substance obtained are then checked on a sheet portion with a surface area of 600 mm$^2$, using the same operating procedure as in example 1. The results obtained up to 56 days are given in FIGS. 3 and 4, which respectively relate to the use of a solution of pH 6.5 and a solution of pH 5 and which represent as a function of time (days) the quantity of copper ($\mu$g) released every day into the solution. These results also confirm the influence of the pH of the solution on the copper quantity released by the substrate.

EXAMPLE 3

This example relates to the production of substrates which can be used as copper-charged intrauterine devices. Acrylic acid is firstly grafted onto an ethylene/vinyl acetate copolymer containing 33% by weight of vinyl acetate and having an average grain size of 0.98 mm.

To this end, 1000 g of EVA copolymer powder are immersed in the following grafting solution:

acrylic acid: 500 ml
soft water: 4000 ml
Mohr's salt: 88 g

It undergoes irradiation by gamma rays using a cobalt 60 source at an irradiation dosage rate of 0.72 mrad/hour for 1½ hours at ambient temperature, whilst maintaining the solution under a nitrogen atmosphere and accompanied by stirring.

Following irradiation, the grafted powder is immediately washed in water heated to 90° C. for 4 hours, followed by drying in a vacuum oven to constant weight.

In this way, a grafted powder is obtained, whose grafting degree is 31.8% by weight of acrylic acid, based on the EVA copolymer powder weight.

The grafted powder is then intimately mixed with 15% by weight of copper powder having an average grain size of 50 microns and this mixture is brought into the form of intrauterine devices by hot injection moulding of the mixture in moulds corresponding to size 0 and size 1 OM-GA-type intrauterine devices. As can be seen from FIG. 5, an intrauterine device (IUD) of this type has an essentially especially shaped frame. It can also be seen that the device corresponding to size 0 has a width of 26 mm and a height of 26 mm, whilst the size 1 device has a width of 35 mm and a height of 35 mm.

The desorption properties of the thus obtained intrauterine devices are then checked:

(a) either by placing the IUD in a glass apparatus with a volume of 5 cm$^3$ in which circulates an isotonic liquid flow of (9 g of NaCl/l, pH 5 or 6.5)

400 cm$^3$/day, the whole apparatus being kept at a temperature of 37° C.;

(b) or by placing the IUD in a container containing 1 liter of the same isotonic solution kept at a temperature of 37° C.

In both cases, the solution is changed or sampled at regular intervals and the quantity of copper in the sample solution is examined.

The results obtained, which are identical in both cases, are given in FIGS. 6, 7, 8 and 9 which graphically show, as a function of time (days) the quantity of copper ($\mu$g) released every day:

(a) by the size 0 IUD in a solution of pH 6.5 (FIG. 6)
(b) by the size 0 IUD in a solution of pH 5 (FIG. 7)
(c) by the size 1 IUD in a solution of pH 6.5 (FIG. 8)
(d) by the size 1 IUD in a solution of pH 5 (FIG. 9).

It can be seen from these drawings that the quantity of copper released every day is stabilised after 10 days at a level of 20 to 30 microgrammes daily and that the influence of the size of the IUD and the pH of the solution are small.

EXAMPLE 4

An ethylene/vinyl acetate copolymer powder containing 33% by weight of vinyl acetate and with a grain size distribution between 0.08 and 0.12 mm is grafted by acrylic acid, 625 g of the EVA copolymer powder being submerged in a grafting solution containing:

310 cm$^3$ of acrylic acid
55 g of Mohr's salt
2500 cm$^3$ of distilled water.

The powder is continuously stirred in the solution and is maintained under a nitrogen atmosphere containing 10 ppm of oxygen and is then irradiated at a dosage rate of 0.72 mrad/hour for 55 minutes at ambient temperature.

The grafted powder is then washed with water and alcohol and is dried under vacuum in an oven.

The degree of grafting of the thus obtained powder is 47% by weight of acrylic acid, based on the initial weight of the copolymer powder (EVA).

100 g of the thus obtained grafted powder is then mixed with 32 g of pulverulent copper acetate having an average grain size of 60 microns. The mixture which is brought into the form of a sheet by compressing it in a mould is then heated at 150° C.

The desorption properties of the sheet obtained are checked on a 30×20×2.5 mm sample weighing 1.751 g. This sample is submerged in two liters of isotonic solution (9% of NaCl), whose pH has been adjusted to 5. The desorption solution is changed at regular intervals and its copper content is determined.

The results obtained are given in FIG. 10 which illustrates, as a function of time (days) the quantity of copper ($\mu$g) released daily by the substrate.

EXAMPLE 5

A polyamide 11 powder of grain size 100 to 125 microns is grafted by butylacrylate using the preirradiation method.

10.74 grammes of polyamide powder are irradiated in a funnel under vacuum using a 3 MeV accelerated electron beam at a dosage of 9 mrad. Still under vacuum, the irradiated powder is brought into contact with 100 cm$^3$ of an alcoholic solution of butyl acrylate (concentration 1/1) for 40 minutes at 70° C. The grafted powder is then washed with alcohol and it is dried under vacuum in an oven.

The degree of grafting of the thus obtained powder is 20% by weight of butyl acrylate based on the initial weight of the polyamide 11 powder.

100 grammes of the thus obtained grafted powder are then mixed with 20 g of active principal, 2-(3-benzoyl-phenyl)-propionic acid (ketoprofen) and the mixture is then brought into the form of a sheet by compressing it in a mould at a temperature of 90° C.

The desorption rate of the active principal is determined on a 30×20×2.5 mm sample taken from the sheet and this sample is submerged in 1 liter of ethyl alcohol TBG.

The ethyl alcohol concentration in the 2-(3-benzoyl-phenyl)-propionic acid is determined at regular intervals.

The desorption rate remains constant for the first 8 hours.

EXAMPLE 6

Under the conditions described in example 1, 10.16 grammes of polyamide 11 powder irradiated at a dosage of 9 mrad under a 3 MeV accelerated electron beam are brought into contact with 100 cm$^3$ of a butyl acrylate solution in ethyl alcohol (concentration 1/1) for 1 hour at 70° C.

the alcohol-grafted powder is then washed and dried under vacuum in an oven. The grafting degree of the thus obtained powder is 40% by weight of butyl polyacrylate, based on the initial weight of the polyamide 11 powder.

EXAMPLE 7

Under the conditions described in example 1 using a butyl acrylate solution in ethyl alcohol (70/30) 10.10 grammes of polyamide 11 powder of grain size between 100 and 125 microns are grafted at 70° C. for 30 minutes.

A grafting degree of 38% by weight of polyacrylate, based on the initial weight of the polyamide 11 powder is obtained.

EXAMPLE 8

Granules of ethylene/vinyl acetate copolymer (EVA) containing 33% vinyl acetate are grafted using a butyl acrylate solution in ethyl alcohol (concentration 25/75).

To bring about grafting the weighed EVA granules are placed in Pyrex glass funnels containing the butyl acrylate solution in ethanol to which is added 1% copper acetate and 0.25% copper powder to inhibitor polymerization of the monomer in solution.

The funnels are degased and then irradiated by gamma rays of cobalt 60 at a dosage rate of 0.2 mrad/h$^{-1}$ at ambient temperature.

The following results were obtained:

| Tests | Grafting solution dose | | | % grafting |
|-------|------|---------|-----|------------|
|       | ABu  | Ethanol |     |            |
| A     | 25   | 75      | 3.4 | 35         |
| B     | 35   | 65      | 3.4 | 43         |
| C     | 45   | 55      | 3.4 | 66         |

100 grammes of thus grafted granules were then mixed with 25 grammes of the active principal 2-(3-benzoyl-phetnyl)-propionic acid, after which the mixture was brought into sheet form by compressing it into a mould at 80° C.

The desorption rate was determined as described in example 1. The desorption rate remains constant for the first 40 days.

EXAMPLE 9

A low density polyethylene powder of grain size 200 to 400 microns is grafted with ethylene glycol acrylate by the preirradiation process. 10.10 grammes of powder are irradiated in a funnel under vacuum using a 3 MeV accelerated electrode beam at a given dosage. Still under vacuum, the irradiated powder is brought into contact with 100 cm³ of the following solution:
50 cm³ of ethylene glycol acrylate
50 cm³ of distilled water
1% by Mohr's salt.
The following results were obtained:

| Sample No | Dose | Temperature | Duration | % grafting |
|---|---|---|---|---|
| 1 | 6.5 mrad | 75° C. | 1h | 90% |
| 2 | 9 mrad | 75° C. | 1h | 109% |
| 3 | 9 mrad | 97° C. | 1h | 75% |

100 grammes of polyethylene powder grafted under the conditions of sample 1 were then mixed with 30 grammes of active principal of the codeine phosphate. The mixture was then brought into the sheet form by compressing it at 40° C.

The desorption rate of the active principal was determined on a 30×20×2.5 mm sample taken from a sheet. This sample was submerged in 1 liter of water at pH 7.4.

The codeine phosphate concentration was determined at regular intervals. The desorption rate remains constant for the first 8 hours.

What is claimed is:

1. A hydrophobic substrate adapted to release therefrom at least one chemical substance comprising, a hydrophobic polymer matrix, first inclusions and second inclusions homogeneously distributed in the polymeric matrix, said first inclusions comprising a polymeric material which is different from the polymer matrix and forms a stable and continuous system in contact with said inclusions, said second inclusions comprising at least one solid state chemical substance.

2. A hydrophobic substrate according to claim 1, wherein the hydrophobic polymer is chosen from the group containing polyvinyl acetates, polyethylenes, polypropylenes, polyamides, ethylene glycol polyterephthalate, polyvinyl chlorides, polyformaldehyde chlorides, polycarbonates, ethylene copolymers, polyethers, polyurethanes, and polyacrylonitriles 3. A hydrophobic substrate according to claim 2 wheren the hydrophobic polymer is a copolymer of polyethylene and vinyl acetate.

4. A hydrophobic substrate according to claim 1, wherein the polymerized compounds are hydrophilic compounds.

5. A substrate according to claim 4, wherein the polymerized compounds are polymers of a hydrophilic monomer chosen from the group containing acrylamide, ethylene glycol acrylate, methylol acrylamide, diacetone acrylamide, maleic acid, acrylic acid, fumaric acid, itaconic acid, propylene glycol acrylate, ethylene glycol methacrylate, methacrylamide, methacrylic acid and propylene glycol methacrylate.

6. A substrate according to claim 4, wherein the chemical substance is a metal or a metal salt.

7. A substrate according to claim 6, wherein the chemical substance is chosen from the group containing copper and copper acetate.

8. A substrate according to claim 4, wherein the substance is codeine phosphate.

9. A hydrophobic substrate according to claim 1, wherein the polymerized compounds are hydrophobic compounds.

10. A substrate according to claim 9, wherein the polymerized compounds are polymers of a hydrophobic monomer chosen from the group containing ethyl acrylate, butyl acrylate, isobutyl acrylate, hexyl, acrylate, heptyl acrylate, ethyl methacrylate, butyl methacrylate, isobutyl methacrylate, hexyl methacrylate, heptyl methacrylate, and acrylonitriles.

11. A substrate according to claim 9, wherein the substance is 2-(3-benzoylphenyl) propionic acid.

12. A process for the preparation of a hydrophobic substrate able to release a chemical substance, wherein it comprises:
   (a) forming inclusions of polymerized compounds in a hydrophobic polymer powder by grafting onto the latter a monomer of a different type to the said hydrophobic polymer
   (b) homogeneously mixing the grafted powder obtained in this way with a powder of the said substance and
   (c) bringing the mixture into the form of a substrate by hot shaping it.

13. A process according to claimm 12, wherein the monomer is a hydrophilic monomer.

14. A process according to claim 13, wherein the substance is codeine phosphate.

15. A process according to claim 13, wherein the substance is a metal or a metal salt.

16. A process according to claim 15, wherein the substance is chosen from the group containing copper and copper acetate.

17. A process according to claim 13, wherein the hydrophilic monomer is chosen from the group containing acrylamide, ethylene glycol acrylate, methylol acrylamide, diacetone acrylamide, maleic acid, acrylic acid, fumaric acid, itaconic acid, propylene glycol acrylate, ethylene glycol methacrylate, methacrylamide, methacrylic acid and propylene glycol methacrylate.

18. A process according to claim 12, wherein the monomer is selected from the group consisting of ethyl acrylate, butyl acrylate, isobutyl acrylate, hexyl acrylate, heptyl acrylate, ethyl methacrylate, butyl methacrylate, isobutyl methacrylate, hexyl methacrylate, heptyl methacrylate, and acrylonitrile.

19. A process according to claim 18, wherein the substance is 2-(3-benzoylphenyl)-propionic acid.

20. A process according to claim 12, wherein the monomer is grafted onto the hydrophobic polymer powder by subjecting said powder submerged in a solution of the monomer containing a polymerization inhibitor to irradiation by means of ionizing rays.

21. A process according to claim 20, wherein the degree of grafting of the monomer on the hydrophobic polymer is checked by regulating the temperature and monomer concentration of the solution, the irradiation dosage rate and the irradiation duration.

22. A process according to claim 12, wherein the powder of the substance has a grain size below that of the powder of the grafted hydrophobic polymer.

23. A process according to claim 12, wherein hot shaping is performed by injection moulding, extrusion or compression moulding.

24. A process according to claim 12, wherein after hot shaping, the substrate obtained undergoes cross-linking by means of ionizing rays.

25. Process according to claim 12, wherein the hydrophilic polymer is chosen from the group containing polyvinyl acetates, polyethylenes, polypropylenes, polyamides, ethylene glycol polyterephthalates, polyvinyl chlorides, polyformaldehyde chlorides, polycarbonates, ethylene copolymers, polyethers, polyurethanes, polyacrylonitriles and copolymers of polyethylene and vinyl acetate.

26. Use of a hydrophobic substrate according to claim 4, as an intrauterine device which can release an active substance into the uterus.

* * * * *